United States Patent
Särelä

Patent Number: 5,605,146
Date of Patent: Feb. 25, 1997

[54] METHOD AND AN ARRANGEMENT IN CONNECTION WITH VAPORIZING AN ANAESTHETIC

[75] Inventor: Antti Särelä, Espoo, Finland

[73] Assignee: Instrumentarium OY, Finland

[21] Appl. No.: 346,545

[22] Filed: Nov. 29, 1994

[30] Foreign Application Priority Data

Nov. 29, 1993 [FI] Finland ........................ 935311

[51] Int. Cl.⁶ .................................. A61M 16/18
[52] U.S. Cl. ................... 128/203.12; 128/203.14; 128/203.26; 128/204.14
[58] Field of Search ............. 128/204.14, 200.14, 128/200.24, 200.22, 203.12, 203.14, 203.16, 203.17, 203.25, 203.26, 203.27, 204.13

[56] References Cited

U.S. PATENT DOCUMENTS

| | | | |
|---|---|---|---|
| 4,019,511 | 4/1977 | Choporis et al. | 128/203.26 |
| 4,026,283 | 5/1977 | Benjavich et al. | 128/203.26 |
| 4,059,657 | 11/1977 | Hay | 128/203.25 X |
| 5,168,866 | 12/1992 | Montgomery | 128/203.12 |
| 5,265,596 | 11/1993 | Sauze | 128/205.24 |

FOREIGN PATENT DOCUMENTS

| | | |
|---|---|---|
| 438218 | 7/1991 | European Pat. Off. |
| 454390 | 10/1991 | European Pat. Off. |
| 545567 | 6/1993 | European Pat. Off. |
| 2053793 | 4/1971 | France |
| 64328 | 9/1892 | Germany |
| 4105370 | 8/1992 | Germany |
| 4111138 | 10/1992 | Germany |
| 2253149 | 9/1992 | United Kingdom |

OTHER PUBLICATIONS

Allen B. Dobkin and Andrew R. Hunter, *Vaporisers for inhalation anaesthetics*, 1979 Elsevier, Biomedical Press, North Holland, p. 320.

Primary Examiner—V. Miller
Assistant Examiner—Eric P. Raciti
Attorney, Agent, or Firm—Andrus, Sceales, Starke & Sawall

[57] ABSTRACT

The invention relates to a method and an arrangement in connection with vaporizing an anaesthetic. The invention comprises a vaporizing chamber for an anaesthetic liquid to be vaporized and means for mixing vaporized anaesthetic with fresh gas and delivering the mixture to be inhaled by a patient. To stabilize the temperature of the anaesthetic liquid in the vaporizing situation, an air flow enhancing the transfer of heat energy between the anaesthetic liquid within the vaporizing chamber and air outside the vaporizing chamber is applied to at least one exterior surface of the vaporizing chamber in forced circulation.

38 Claims, 1 Drawing Sheet

METHOD AND AN ARRANGEMENT IN CONNECTION WITH VAPORIZING AN ANAESTHETIC

BACKGROUND OF THE INVENTION

1. Field of the Invention

The present invention relates to a method in connection with vaporizing an anaesthetic, in which an anaesthetic vaporized in a vaporizing chamber is mixed with fresh gas and delivered to be inhaled by a patient. The invention also relates to an arrangement in connection with vaporizing an anaesthetic.

2. Description of the Related Art

The invention thus relates to anaesthesia and particularly to vaporizing a liquid anaesthetic. The vaporized anaesthetic is mixed with fresh gas, which may comprise oxygen and nitrous oxide. Fresh gas is obtained from the hospital gas supply system by forming a mixture of various gases, for instance. The mixed flow comprised of fresh gas and vaporized anaesthetic is administered for the patient to inhale when anaesthetizing the patient, for instance.

Vaporization of a liquid anaesthetic consumes thermal energy in a similar manner as vaporization of other liquid substances does. In conventional vaporizers previously known in the field, sufficient heating energy is transmitted to the liquid by convection from the constructions of the vaporizer and from ambient air. The temperature of the vaporizer, and of the anaesthetic contained therein, tends to decrease in vaporization. When the temperature of the anaesthetizing liquid drops, also the pressure of vapour evaporated therefrom, and simultaneously its concentration within the vaporizer, decreases. This would cause the concentration of the administered anaesthetic to decrease, if no compensation according to temperature were carried out.

A new anaesthetic, desflurane, has recently been developed in the field. The physical and physiological properties of desflurane are markedly different from those of conventional anaesthetics. Desflurane has a boiling point of 23.5° C. at normal air pressure, while that of other anaesthetics is about 50° C. Furthermore, desflurane has a much stronger dependency of vapour pressure on temperature at normal operating temperatures than the anaesthetics previously employed. For example at 20° C., desflurane has a vapour pressure of 32 mmHg/°C. whilst that of halothane, one of the previously used anaesthetics, is 10 mmHg/°C. Moreover, the ranges of use that are possible for desflurane are broader, 0–18%, than those for previously employed anaesthetics, which are 0–5%. The above factors require new methods for safe and reliable vaporization of desflurane.

In the conventional vaporizer of the by-pass type, part of the fresh gas is passed via a conduit to a vaporizing container containing an anaesthetic liquid, and part of it bypasses the container. The vapour saturated with anaesthetic issuing from the container is recombined with the by-pass flow, and the mixture is then delivered to the patient. The concentration of anaesthetic may be varied by adjusting the distribution ratio with a valve, for example. Also temperature compensation is based on varying the distribution ratio as a function of temperature. When the temperature and concurrently the vapour pressure of the anaesthetic decreases, a larger portion of the fresh gas flow is passed through the container containing anaesthetic, and when the temperature rises, the flow through the container is diminished.

If desflurane is vaporized with the conventional by-pass method, temperature changes are more difficult to compensate for than with previously employed anaesthetics. This is due to the following factors:

Desflurane exhibits a high dependency of vapour pressure on temperature, as previously stated. If the liquid temperature is below the boiling point, the temperature of the anaesthetic liquid decreases when the anaesthetic is vaporized, and simultaneously the anaesthetic concentration of the vapour contained within the vaporizing container decreases. This decrease in concentration as a function of temperature is about three times as high with desflurane as with other anaesthetics.

Desflurane concentrations in fresh gas to be administered to a patient are about four times those of conventional anaesthetics. In consequence, the desflurane vaporizer must be capable of producing four times the quantity of vapour needed with other vaporizers. Since the vaporization heat of desflurane is of the same order as that of other anaesthetic agents, also the heat energy required for vaporization is about four times that required for the conventional anaesthetic agents. If no exterior energy were supplied to the vaporizing container, also the temperature drop produced by vaporization would be about four times the temperature drop encountered with conventional agents.

From the above it can be seen that the temperature of desflurane drops more rapidly than that of other anaesthetics, and that the temperature drop has a more drastic effect on the concentration than in vaporizers for other anaesthetics.

In principle, three solutions have been developed for vaporizing desflurane. In the first, the liquid desflurane is electrically heated to a certain temperature above the boiling point, and the temperature is maintained constant by active heating. In that case, the vapour to be administered consists entirely of desflurane. Since the pressure in the vaporizing chamber increases with the increase of temperature, anaesthetic can be supplied directly from the container without any fresh gas flow through the container. Such an arrangement is disclosed in European published application 0 454 390 and British published application 2 253 149, for instance.

In the above method, no compensation of temperature changes is needed, as the temperature is maintained constant and the vapour to be administered consists entirely of anaesthetic. The greatest drawback of the method is the high consumption of electrical energy. As the liquid has a temperature above ambient, all energy must be supplied to the vaporizer by electrical means to produce a sufficient amount of vapour and also to maintain the temperature in the vaporizer constant, since the entire vaporizer is cooled to ambient air. Furthermore, on account of the heating the vaporization cannot be commenced until a sufficient vaporizer temperature has been achieved.

In another known arrangement, an anaesthetic liquid is cooled below the boiling point, and the temperature of the liquid is maintained constant during vaporization by active cooling and heating. In this arrangement, the conventional by-pass method must be used to administer the anaesthetic. Such an arrangement is disclosed in U.S. Pat. No. 5 168 866, for example.

In the above prior art method, the temperature effects of desflurane are managed by actively maintaining the temperature constant. The problems of the method are essentially the same as in the above method based on heating. Cooling consumes even more energy than heating, since the efficiency of cooling elements is poor. It is further to be noted that the vaporizer cannot be operated during cooling.

A third prior art arrangement is disclosed in European published application 0 545 567, for example. This arrangement is a conventional by-pass vaporizer. The method does not stabilize the liquid temperature at all; by determining the gas flow issuing from the vaporizing chamber and also its anaesthetic concentration in some way, the anaesthetic can be dosed by regulating the flow ratio. The temperature of the anaesthetic is not controlled in this method.

The above method manages the temperature effects of desflurane by measuring the physical status of the system, and the flow through the vaporizing chamber is regulated on the basis of the measuring results. The problem with this known method consists in the high requirements set on the temperature measuring accuracy and the wide control range required for the flow ratio, resulting from the above-stated temperature effects of desflurane.

SUMMARY OF THE PRESENT INVENTION

It is an object of the present invention to provide a method and an arrangement wherewith the disadvantages of the previously known solutions can be eliminated and an arrangement can be achieved that has low power consumption in comparison with other vaporization arrangements for e.g. desflurane. This has been achieved with the method and arrangement of the invention. The method of the invention is characterized in that an air flow enhancing the transfer of heat energy between the anaesthetic liquid within the vaporizing chamber and air outside the vaporizing chamber is applied to at least one exterior surface of the vaporizing chamber in forced circulation. The arrangement of the invention is characterized in that the arrangement further comprises an apparatus producing a gas flow, adapted to apply a forced air flow enhancing the transfer of heat energy between the anaesthetic liquid within the vaporizing chamber and air outside the vaporizing chamber to at least one exterior surface of the vaporizing chamber.

With the invention, the heat transfer capability of the vaporizing chamber can be substantially improved and simultaneously the power consumption diminished in comparison with the prior art. Furthermore, with the invention the temperature of the anaesthetic liquid in the vaporizing situation is essentially stabilized as compared with the prior art. Thus in vaporization the liquid temperature does not drop as rapidly and drastically as when no air circulation is provided. With the invention, the wide control range for the flow ratio that has previously been required for desflurane can be diminished to be close to the control range for conventional anaesthetics. Thus it is possible to use the same mechanical implements with all anaesthetic agents. As temperature changes are diminished as a result of the invention, also the precision requirements for compensation of the changes are essentially lessened in comparison with the prior art.

BRIEF DESCRIPTION OF THE DRAWING

In the following the invention will be explained in greater detail by means of a preferred embodiment illustrated in the accompanying drawing, in which.

DESCRIPTION OF THE PREFERRED EMBODIMENTS

Figure 1:
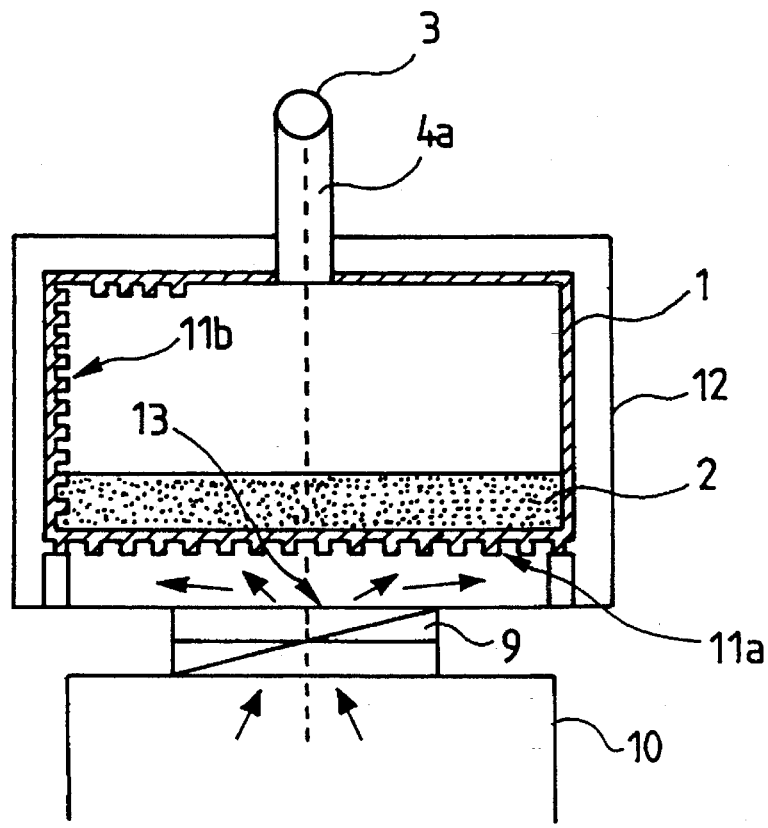
FIG. 1 is a schematic view of a preferred embodiment of the invention.
Figure 2:
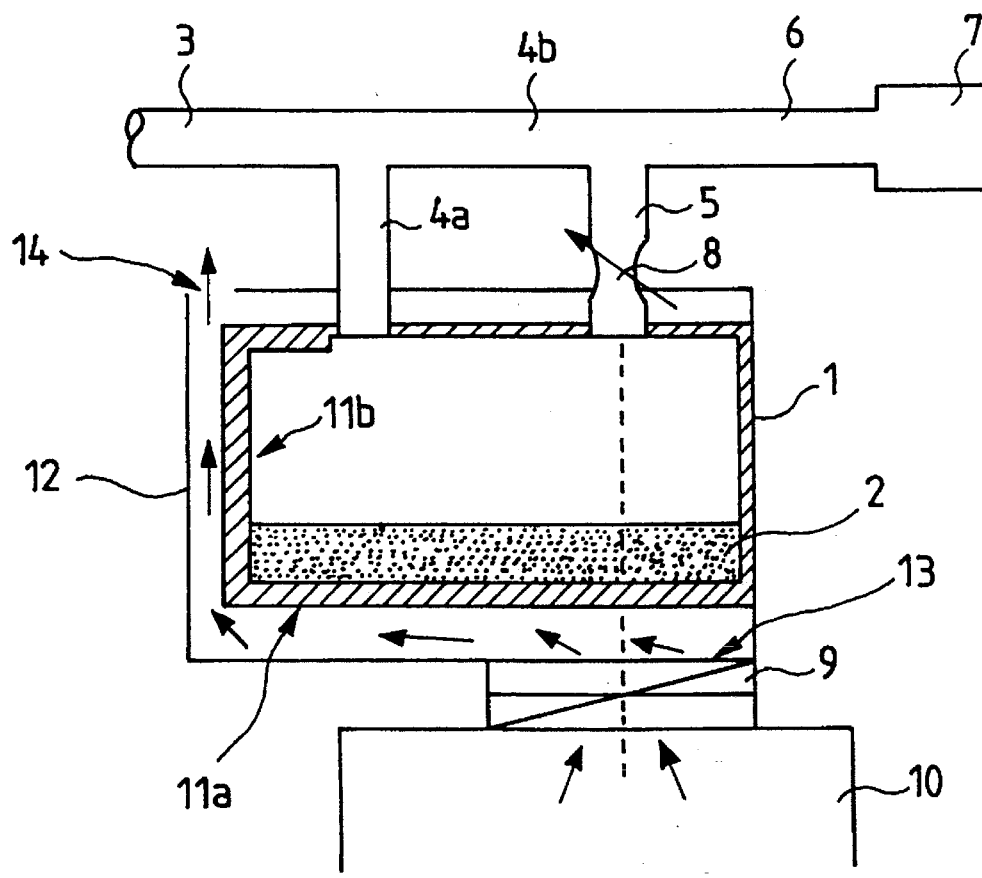
FIG. 2 shows the embodiment of FIG. 1 in a schematic view from another direction.

In the embodiment shown in the drawings, the invention has been implemented in an arrangement according to the third example set out above. In the figures, reference numeral 1 denotes a vaporizing chamber containing an anaesthetic liquid 2. The anaesthetic liquid may ba desflurane, for example. Reference 3 denotes the inlet pipe for fresh gas. The fresh gas inlet pipe 3 consists of two portions 4a and 4b, so that part of the fresh gas flows through pipe branch 4a to the vaporizing chamber 1, and part of it through the other pipe branch 4b past the vaporizing chamber 1. Reference 5 denotes a flow pipe through which the mixture of vaporized anaesthetic and fresh gas is conveyed out from the vaporizing chamber 1 and passed through the second pipe branch 4b into the fresh gas flow bypassing the vaporizing chamber 1. Reference 6 denotes piping through which the mixture formed as above is administered for inhalation by a patient. The patient is diagrammatically sketched in FIG. 2 at reference 7. The anaesthetic concentration in the gas supplied to the patient for inhalation can be adjusted for example with a valve 8 provided in the flow pipe 5. The distribution ratio of the fresh gas passing through the vaporizing chamber can be varied by regulating the valve 8, as set out previously.

The above features constitute fully conventional art to the skilled man, and thus they will not be explained more closely in this context, but reference is made herein to the above publications, for instance, in which such features have been described.

What is essential in the invention is that it comprises an apparatus 9 producing a gas flow, adapted to apply a forced air flow enhancing the transfer of heat energy between the anaesthetic liquid 2 within the vaporizing chamber and air outside the vaporizing chamber to at least one exterior surface of the vaporizing chamber 1. This forced circulation substantially diminishes the thermal resistance between the anaesthetic liquid 2 within the vaporizing chamber 1 and the ambient air as compared with the prior art. The air flow may be applied to one or several exterior surfaces of the vaporizing chamber; for example, an air flow may be applied to the bottom surface of the vaporizing chamber. It has been found that with the present invention, the thermal resistance referred to above may be diminished at least by the factor four, which means that the temperature difference required for heat transfer diminishes to a quarter as compared with the prior art. The thermal resistance can be further diminished by suitably modifying the vaporizing chamber 1. Examples of suitable modifications are the provision of ribbing or the like, 11a, 11b, on the exterior surface, interior surface or both surfaces of the vaporizing chamber. The ribbing or the like may also be provided on a part of a surface, etc. The thermal resistance properties may also be altered by means of the manufacturing material of the vaporizing chamber. Examples of useful materials are heat-conductive metals and the like.

In the embodiment shown in the figures, the apparatus 9 producing a gas flow is adapted to suck in air from the exterior 10 of the vaporizing chamber, e.g. from within the anaesthetic apparatus, and to blow it onto the surfaces of the anaesthetic chamber, as set forth above. The apparatus 9 producing the gas flow may be e.g. a fan, extractor or other corresponding apparatus. The passage of air is denoted by arrows in the figures.

Furthermore, it is advantageous in view of the final result that the vaporizing chamber 1 is fitted within a casing 12 provided with an air inlet 13 and air outlet 14. The walls of the casing 12 are adapted to provide, together with the exterior surfaces of the vaporizing chamber 1, a flow passage for air, as will be apparent from the figures. Through this flow passage, the air from the fan 9 (for example) is made to flow in forced circulation in the desired manner relative to the vaporizing chamber.

With the invention, the heat transfer capability of the vaporizing chamber can be substantially improved, and simultaneously the temperature of the anaesthetic liquid in the vaporizing situation can be stabilized, which offers considerable advantage over the prior art, as explained previously. It is essential to note that in the invention, energy transfer sufficient for vaporization can be arranged in a very advantageous way by using an inexpensive fan consuming very little energy. The fan may be e.g. of a type consuming about 2 watts, and thus there is a clear difference to the heating or cooling arrangements previously employed. A suitable air quantity, applied to the exterior surface or surfaces of the vaporizing chamber, may be e.g. in the range 0.5–5 $m^3$/min. A further advantage is afforded by the fact that the apparatus, e.g. a fan, which produces a gas flow and which is an essential element of the invention, may if required be positioned stationarily within the body of the anaesthetic apparatus, thus avoiding provision of an electrical connection to a detachable vaporizing chamber. It is evident, however, that the fan may also be incorporated as part of the vaporizing chamber, if such a solution is considered to be practical. A further advantage of the above fan arrangement is that the waste heat generated in the electronic system of the arrangement, e.g. within the anaesthetic apparatus, can if necessary be used to heat the vaporizing chamber. It is to be noted, however, that in using the invention the heat contained in indoor air is in most cases sufficient. In other words, in most situations all advantages described above are achieved without any extra heating. It is naturally also possible to use existing heat sources, as set out above, or even to use a separate heater, such as a heating resistance, to heat the air to be blown onto the surfaces of the vaporizing chamber.

The embodiment described above is in no way intended to restrict the invention, but the invention may be modified freely within the scope of the claims. Thus it is evident that the arrangement of the invention or its details need not necessarily be precisely as set out in the drawings, but other solutions are possible as well. Even though the starting-point of the above embodiment is that the anaesthetic liquid is desflurane, it is fully possible to implement the invention to conventional anaesthetics as well. In applying the invention to conventional anaesthetics, it is to be noted that the thermal stability of the vaporizing chamber is improved in comparison with the previously employed solutions, since the temperature change in vaporization is smaller. The ribbing on the vaporizing chamber may be implemented by any suitable means. The ribs may be elongated, stud-like, various combinations, etc. The ribbing may be provided either on all surfaces of the vaporizing chamber or at least on some of them. Neither is the invention restricted in any way to the by-pass principle shown in the figure, but it may be applied to other known principles as well.

I claim:

1. A method for providing a quantity of heat to a low temperature boiling point liquid anaesthetic to compensate for temperature reductions resulting from vaporization of such a liquid anaesthetic and to stabilize the temperature of the anaesthetic and the generation of a gaseous anaesthetic from the liquid anaesthetic, the vaporization occurring in an anaesthetic containing chamber having a wall capable of transferring heat, said method consuming low amounts of power and comprising the step of:

forcing the passage of 0.5–5 $m^3$/min. of ambient air along the wall of the chamber to transfer, from the air to the liquid anaesthetic, a quantity of heat that stabilizes the generation of gaseous anaesthetic from the liquid anaesthetic by vaporization of the latter.

2. The method as claimed in claim 1 further defined as forcing the passage of air along the wall of the chamber by means of a fan.

3. The method as claimed in claim 1 wherein the chamber forms part of an anaesthesia apparatus having heat generating components and wherein the step of the method is further defined as passing air heated by said components along the wall.

4. The method as claimed in claim 1 further defined as a method of providing a quantity of heat to a liquid anaesthetic having a boiling point in or near the generally encountered range of room temperatures.

5. The method as claimed in claim 1 further defined as a method of providing a quantity of heat to a liquid anaesthetic comprising desflurane.

6. The method as claimed in claim 1 further defined as forcing the passage of air along a wall formed to enhance the transfer of heat.

7. The method as claimed in claim 6 further defined as forcing the passage of air along a wall having ribs on at least a portion of at least one surface thereof.

8. The method as claimed in claim 7 further defined as forcing the passage of air along a wall having ribs on at least a portion of two surfaces thereof.

9. A method of administering an anaesthetic to a patient, the anaesthetic administered to the patient being obtained from a vaporizable liquid anaesthetic having a low temperature boiling point, said method comprising the steps of:

providing a main flow stream of breathable gas from a gas source means to the patient;

providing a chamber containing the vaporizable, liquid anaesthetic, said chamber having a wall capable of transferring heat;

vaporizing the liquid anaesthetic to form a gaseous anaesthetic in the chamber;

forcing the passage of 0.5–5 $m^3$/min. of ambient air along the wall of the chamber to transfer, from the air to the liquid anaesthetic, a quantity of heat that compensates for vaporization induced temperature reductions in the liquid anaesthetic and that stabilizes the vaporization of the liquid anaesthetic to the gaseous anaesthetic;

diverting a portion of the main flow stream of breathable gas through the chamber to entrain the gaseous anaesthetic;

returning the diverted portion to the main flow stream; and administering the main flow stream of breathable gas containing the anaesthetic to the patient.

10. The method as claimed in claim 9 further defined as forcing the passage of air along the wall of the chamber by means of a fan.

11. The method as claimed in claim 9 wherein the chamber forms part of an anaesthesia apparatus having heat generating components and wherein the step of the method is further defined as passing air heated by said components along the wall.

12. The method as claimed in claim 9 further defined as a method of providing a quantity of heat to a liquid anaesthetic having a boiling point in or near the generally encountered range of room temperatures.

13. The method as claimed in claim 9 further defined as a method of providing a quantity of heat to a liquid anaesthetic comprising desflurane.

14. The method as claimed in claim 9 further defined as forcing the passage of air along a wall formed to enhance the transfer of heat.

15. The method as claimed in claim 14 further defined as forcing the passage of air along a wall having ribs on at least a portion of at least one surface thereof.

16. The method as claimed in claim 15 further defined as forcing the passage of air along a wall having ribs on at least a portion of two surfaces thereof.

17. Apparatus for providing a quantity of heat to a low temperature boiling point liquid anaesthetic to compensate for temperature reductions resulting from vaporization of the liquid anaesthetic and to stabilize the temperature of the anaesthetic and the generation of a gaseous anaesthetic from the liquid anaesthetic, said apparatus comprising:

a chamber containing the liquid anaesthetic and gaseous anaesthetic generated therefrom, said chamber having a wall capable of transferring heat, said chamber having an inlet and an outlet for passing a gas flow stream through said chamber to entrain the gaseous anaesthetic; and means forcing the passage of 0.5–5 $m^3$/min. of ambient air along the wall of the chamber to transfer, from the air to the liquid anaesthetic, a quantity of heat that stabilizes the generation of gaseous anaesthetic from the liquid anaesthetic by vaporization of the latter in the chamber.

18. The apparatus as claimed in claim 17 wherein said means forcing the passage of air along the wall comprises a fan.

19. The apparatus as claimed in claim 17 wherein said means forcing the passage of air along the wall is integrally mounted with said chamber.

20. The apparatus as claimed in claim 17 wherein said means forcing the passage of air along the wall is separably mounted to said chamber.

21. The apparatus as claimed in claim 17 further comprising a casing for receiving said chamber, said casing having an air inlet coupled to said means forcing the passage of air and having an air outlet, said casing forming, together with the exterior of said chamber, a flow passage for the ambient air.

22. The apparatus as claimed in claim 17 wherein the chamber forms part of an anaesthesia apparatus having heat generating components and wherein said ambient air forcing means comprises means forcing the passage of air heated by said components along said wall.

23. The apparatus as claimed in claim 17 wherein said chamber is further defined as containing a liquid anaesthetic comprising desflurane.

24. The apparatus as claimed in claim 17 wherein said chamber is further defined as containing a liquid anaesthetic having a boiling point in or near the generally encountered range of room temperatures.

25. The apparatus as claimed in claim 17 wherein said chamber wall is formed to enhance the transfer of heat.

26. The apparatus as claimed in claim 25 wherein said chamber wall has ribs on at least a portion of at least one surface thereof.

27. The apparatus as claimed in claim 26 wherein said wall has ribs on at least a portion of two surfaces thereof.

28. Apparatus for administering an anaesthetic entrained in a breathable gas to a patient, said breathable gas being supplied by a gas source means, said apparatus comprising:

means connectable to said gas source means and providing a main flow stream of breathable gas from the gas source means to the patient;

a chamber containing a vaporizable, liquid anaesthetic having a low temperature boiling point, and gaseous anaesthetic generated therefrom, said chamber having a wall capable of transferring heat and having an inlet and an outlet;

means coupled to said chamber inlet and outlet for diverting a portion of the main flow stream of breathable gas through the chamber to entrain the gaseous anaesthetic; and means for forcing the passage of 0.5–5 $m^3$/min. of ambient air along the wall of the chamber to transfer, from the air to the liquid anaesthetic, a quantity of heat that compensates for vaporization induced temperature reductions in the liquid anaesthetic and that stabilizes the generation of gaseous anaesthetic from the liquid anaesthetic by vaporization of the latter.

29. The apparatus as claimed in claim 28 wherein said chamber is further defined as containing a liquid anaesthetic comprising desflurane.

30. The apparatus as claimed in claim 28 wherein said means forcing the passage of air along the wall comprises a fan.

31. The apparatus as claimed in claim 28 wherein said means forcing the passage of air along the wall is integrally mounted with said chamber.

32. The apparatus as claimed in claim 28 wherein said means forcing the passage of air along the wall is separably mounted to said chamber.

33. The apparatus as claimed in claim 28 further comprising a casing for receiving said chamber, said casing having an air inlet coupled to said means for forcing the passage of air and having an air outlet,, said casing forming, together with the exterior of said chamber, a flow passage for the ambient air.

34. The apparatus as claimed in claim 28 wherein the chamber forms part of an anaesthesia apparatus having heat generating components and wherein said ambient air forcing means comprises means forcing the passage of air heated by said components along said wall.

35. The apparatus as claimed in claim 28 wherein said chamber is further defined as containing a liquid anaesthetic having a boiling point in or near the generally encountered range of room temperatures.

36. The apparatus as claimed in claim 28 wherein said chamber wall is formed to enhance the transfer of heat.

37. The apparatus as claimed in claim 36 wherein said chamber wall has ribs on at least a portion of at least one surface thereof.

38. The apparatus as claimed in claim 37 wherein said wall has ribs on at least a portion of two surfaces thereof.

\* \* \* \* \*